United States Patent [19]
Ducharme et al.

[11] Patent Number: 5,416,588
[45] Date of Patent: May 16, 1995

[54] SMALL MODULATION ELLIPSOMETRY

[75] Inventors: Stephen P. Ducharme, Lincoln, Nebr.; Hassanayn M. El Hajj, Las Palmas De G.C., Spain; Blaine D. Johs; John A. Woollam, both of Lincoln, Nebr.

[73] Assignee: The Board of Regents of the University of Nebraska, Lincoln, Nebr. ; a part interest

[21] Appl. No.: 284,284

[22] Filed: Aug. 2, 1994

Related U.S. Application Data

[63] Continuation of Ser. No. 994,197, Dec. 21, 1992, abandoned.

[51] Int. Cl.6 .............................................. G01N 21/21
[52] U.S. Cl. ...................................... 356/369; 250/225
[58] Field of Search .............................. 356/364–370, 356/381, 382; 250/225; 359/246, 249, 252, 278, 279, 281, 284–287

[56] References Cited

U.S. PATENT DOCUMENTS

| 3,594,085 | 7/1971 | Wilmanns | 356/369 |
| 3,734,625 | 5/1973 | Aagard | 356/369 |
| 3,981,587 | 9/1976 | Gievers | 356/368 |
| 4,053,232 | 10/1977 | Dill et al. | 356/369 |
| 4,306,809 | 12/1981 | Azzam | 356/369 |
| 4,585,348 | 4/1986 | Chastang et al. | 356/369 |
| 4,872,758 | 10/1989 | Miyazaki et al. | 356/382 |
| 4,953,980 | 9/1990 | DeVolk et al. | 356/367 |

Primary Examiner—Hoa Q. Pham
Attorney, Agent, or Firm—Vincent L. Carney

[57] ABSTRACT

In an ellipsometer, a phase-modulated, polarized light beam is applied to a sample, electrical signals are obtained representing the orthogonal planes of polarization of the light after it has interacted with the sample and the constants of the sample are calculated from the two resulting electrical signals. The phase modulation is sufficiently small so that the calibration errors are negligible. For this purpose, the phase modulator phase modulates the light within a range of no more than ten degrees modulations peak to peak. The two electrical signals are expanded by Fourier analysis and the coefficients thereof utilized to calculate psi and delta.

10 Claims, 2 Drawing Sheets

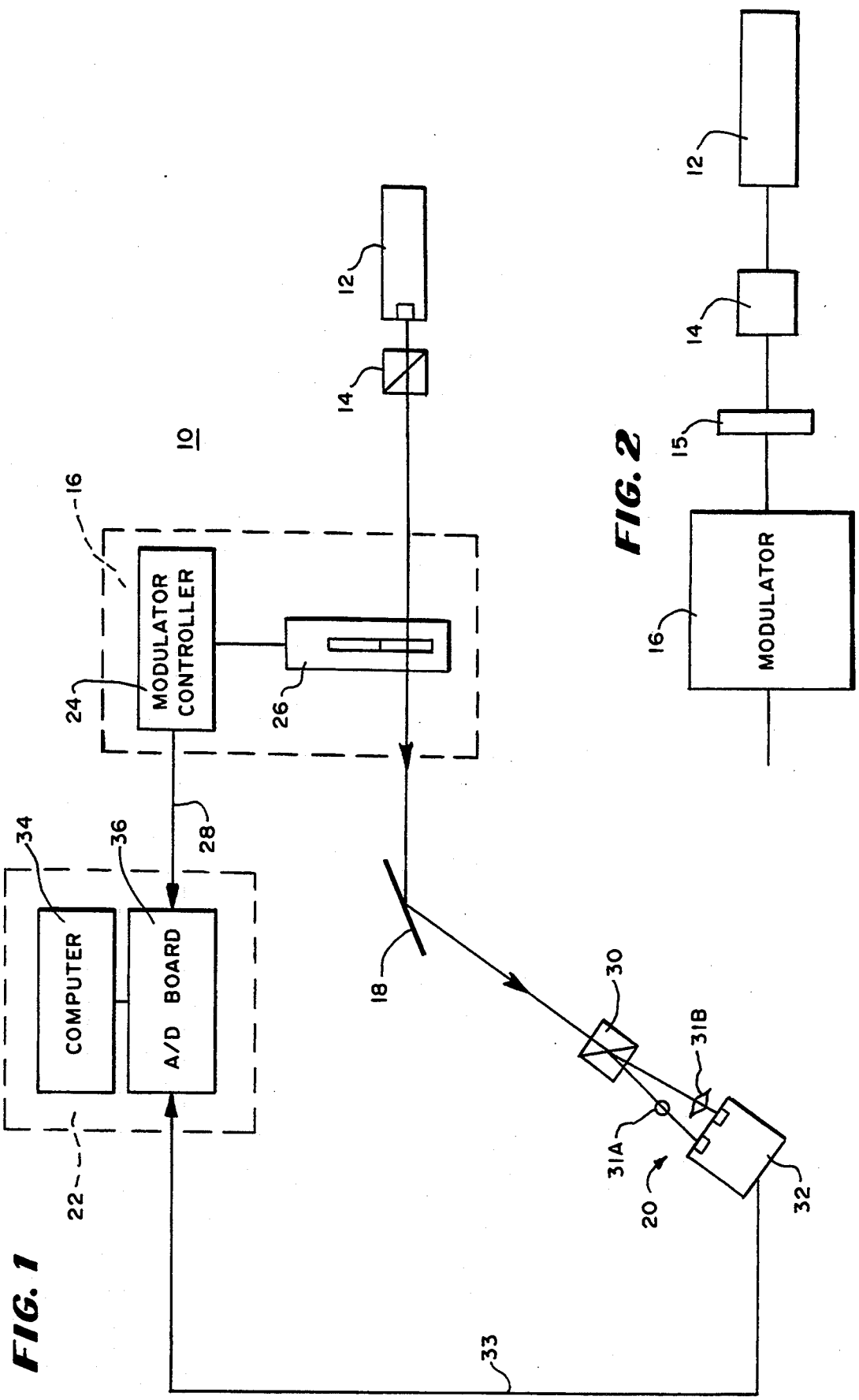

SMALL MODULATION ELLIPSOMETRY

RIGHTS IN THE UNITED STATES GOVERNMENT

This invention was made with Government support under contract NAS8-39327 awarded by NASA. The Government has certain rights in this invention.

This application is a continuation of application Ser. No. 07/994,197, filed Dec. 12, 1992, now abandoned.

BACKGROUND OF THE INVENTION

This invention relates to ellipsometry.

One class of ellipsometers includes a light source, a polarizer, a modulator, an analyzer and at least one intensity detector. In this prior art type of device, the light is modulated and sensed by a photocell. The resulting electric signal is used to calculate psi and delta, which can be done by a number of known techniques including a Fourier expansion of the resulting signal.

In a prior art type of ellipsometer in this class, called a large modulation ellipsometer, the modulator varies the intensity of the beam over a defined range sufficiently large to give an easily measured signal.

This type of ellipsometry has a disadvantage in that the system must be calibrated to take into account nonlinear changes in output signals dependent upon light intensity or polarization state. For example, the photocell output signal in some ranges changes nonlinearly with respect to changes in the intensity of light and the light reflected from diffration gratings, if any are included, change nonlinearly with respect to changes in the phase. The changes in ranges of intensity and polarization state are caused by changes in reflected or transmitted light as the environment of measurement changes.

Because of the need for recalibration with changes in the environment, corrections may need to be made such as in the software to make the necessary corrections or adjustment of voltages or adjustment of amplification level of amplifiers or sensors or attenuation levels of signals from photocells or changes in the angle of the diffraction grating if one is included or in the polarizer. This alignment is generally obtained by measuring the psi and delta of a known environment similar to the one being tested and calibrating the instrument in that known environment.

This disadvantage of prior art type of ellipsometers is especially severe when continuous measurements of time varying quantities are made because of the need to calibrate for different surfaces.

SUMMARY OF THE INVENTION

Accordingly, it is an object of the invention to provide a novel ellipsometry technique.

It is a still further object of the invention to provide a novel ellipsometer capable of measuring time varying changes in surfaces in real time.

It is a still further object of the invention to provide a novel ellipsometric technique which does not require calibration when measuring time varying surfaces over a wide range.

It is a still further object of the invention to provide an ellipsometric technique and instrument in which the calibration constants do not require frequent adjustment.

It is a still further object of this invention to provide an amplitude modulation ellipsometer which uses sufficiently small modulation parameters so that the calibration errors are insignificant.

In accordance with the above and further objects of the invention, an ellipsometer includes a source of light, a polarizer, a modulator and a split analyzer. The sample receives polarized light from the source and reflects or transmits that light with a change in its polarization state. The light is modulated with such a small value as to cause the calibration errors related to changes in the orientation of the polarized light and light intensity insignificant.

A split analyzer: (1) separates the light reflected from or transmitted through the sample into two different mutually orthogonal components, one of which represents light polarized in alignment with the "p" plane and the other of which represents light polarized in alignment with the "s" plane; and (2) connects each component into a different electrical signal. Although the two components have mutually orthogonal polarization, the polarizations are not identical to the "s" and "p" polarizations relative to the sample. The separate electrical signals from two light beams are utilized to determine psi and delta.

The amount of modulation that renders the calibration constants insignificant is usually in the order of three or four degrees, but always under ten degrees and preferably under 5 degrees of phase modulation. The amount can be determined for specific environments from a Jones matrix by deciding on the degree of error that is tolerable and setting the angles of the sines and cosines below that amount for modulation. For the purpose of this specification, the amount of modulation is considered as the number of degrees of a complete wavelength of light. Amplitude modulation may also be used to reduce noise by synchronous detection.

This ellipsometric technique has several advantages, such as: (1) it can measure a changing environment, such as for example a surface that is in use such as in a spacecraft or the like; and (2) there is less time necessary for calibrating the instrument to different surfaces.

DISCRIPTION OF THE DRAWINGS

The above noted and other features of the invention will be better understood from the following detailed description when considered with reference to the accompanying drawings, in which:

FIG. 1 is a block diagram of one embodiment of small modulation ellipsometer in accordance with the invention;

FIG. 2 is a fragmentary block diagrammatic view of a modification of the ellipsometer of FIG. 1 that forms a second embodiment.

DETAILED DESCRIPTION

Figure 3:
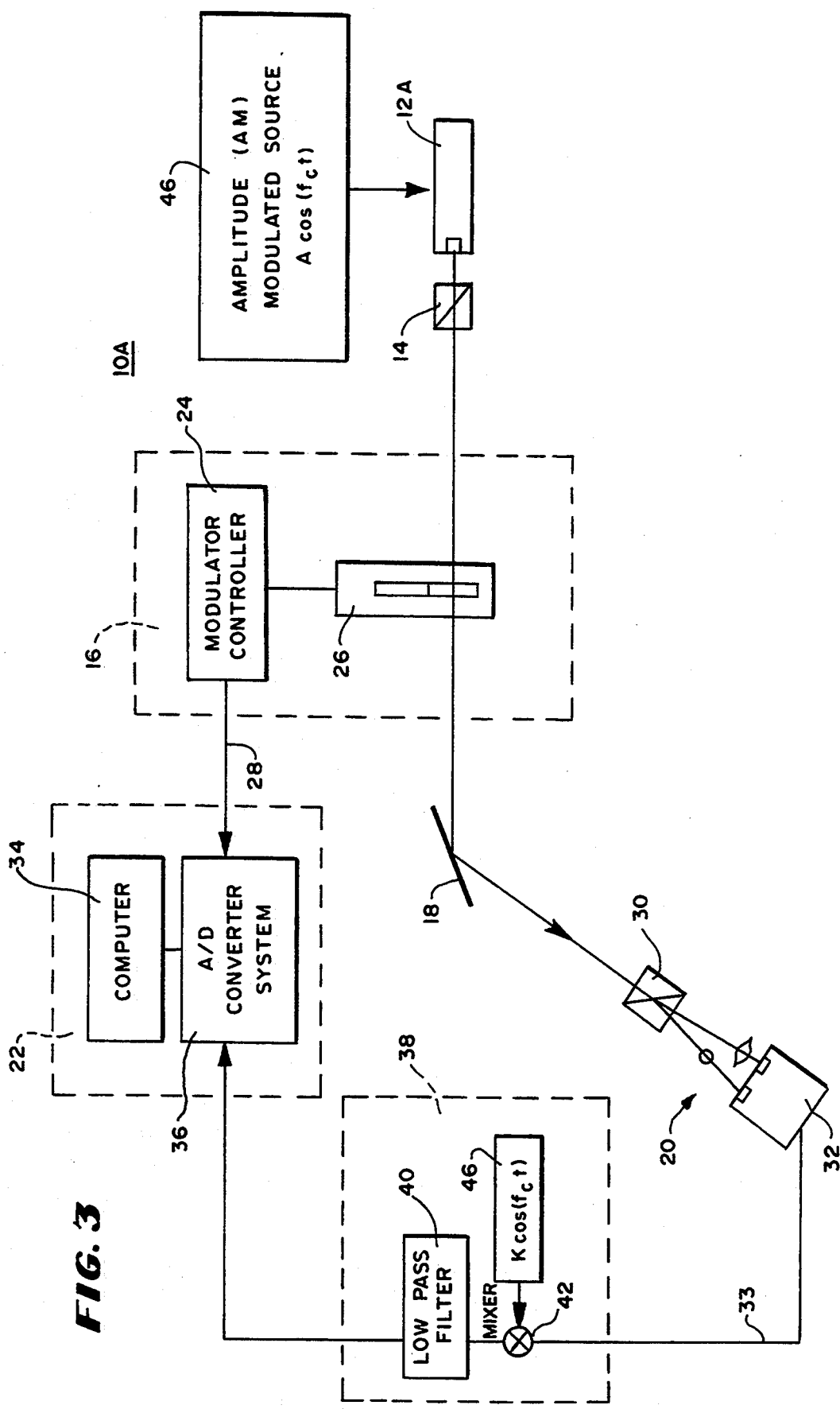
FIG. 3 is a block diagram of a third embodiment of ellipsometer in accordance with the invention.

In FIG. 1, there is shown one embodiment of small modulation ellipsometer 10 called a polarizer-modulator-sample-analyzer having a light source 12, a polarizer 14, a modulation system 16, a dual analyzer 20 and a harmonic component detector 22. Light from the source 12 passes through the polarizer 14 which produces a linear polarization state. The polarized light passes through the modulation system 16 which alters the polarization state of the light at a high ac frequency. The modulation amplitude and thus the magnitude of the change in polarization state is kept sufficiently small to cause the calibration constants to be negligible as determined by the appropriate Jones matrix analysis of the system.

To obtain signals representing the nature of the surface of a sample 18, the polarized light is caused to interact with the sample 18 such as being reflected from the sample 18 or transmitted through the sample 18. It is shown as being reflected from the sample in FIG. 1. The polarized light is altered in state by the delta and psi of the sample and the altered polarization state is passed through an analyzer, such as a Wollaston prism split analyzer, to separate the orthogonally polarized components of the beam. The orthogonally polarized components of the beam of light are sensed and used to determine delta and psi.

Before converting the beams of light to electrical signals, the beam of light incident on the sample 18 or the beams of light resulting from it at the Wollaston prism split analyzer are phase modulated. The modulation in the preferred embodiment occurs after the the beam of light passes through the polarizer 14 and before it engages the sample 18 but the beam may be modulated at any location along its path up to the time it is split in the split analyzer or the beams of light may be synchronously modulated after being split and before being converted to electrical signals. For this purpose, the modulation system 16 includes a modulator controller 24 and a quartz rod 26 or other phase modulator which is vibrated to delay and advance the light waves as they pass through it to the sample 18.

The modulator controller 24 causes vibration of the quartz rod 26 at a relatively high frequency but only through a phase angle somewhere between a fraction of a degree and ten degrees and preferably under five degrees. The exact value is chosen to render the effect of calibration constants caused by nonlinear characteristics of components such as the photodiodes to be negligible. This can be determined from a Jones matrix.

To obtain two electrical signals, each representing a different one of the two orthogonal planes of polarization of the light after leaving the sample, the dual analyzer 20 includes a split analyzer 30 and two sensors 32. The split analyzer 30 separates each of the orthogonally polarized components of the beam leaving the sample into a separate one of two beams. One such beam splitter is a Wollaston prism split analyzer 30. The two photodetectors 32 each receive only light in its corresponding orthogonal polarized plane. Each of the photodetectors shown at 32 is connected to a different analog to digital converter within the harmonic component detector 22.

The harmonic component detector 22 includes the computer 34 and an analog to digital converter system 36 which receives outputs from two conductors, each of the two conductors shown as a single line 33 in FIGS. 1 and 3 being electrically connected to a different one of the photoelectric devices in the dual photodetectors 32.

The computer 34 computes the Fourier series using standard program software and may be any suitable type of computer or microprocessor capable of making such a calculation. The A/D board 36 includes two analog to digital converters, each connected to a different one of the two conductors shown as the line 33.

A Fourier expansion of the two signals would result in a signal of the type indicated by equation 1 or equation 2 where the angular frequency is omega, $V_a$ is the signal from one of the photosensors, $V_b$ is a signal from the other photosensor, small t is time and each term represents one harmonic of the harmonic expansion in terms of voltage.

The expansion may be formed by any of several means although in the preferred embodiment a Fourier expansion is obtained using a microprocessor and the program provided hereinafter. Commercial Fourier transform programs that are suitable are available as well. Alternate hardware is available for such a Fourier expansion such as by filtering the different frequency components in separate filters, separating the sine and cosine functions for each frequency by phase detection and gating the functions to an output conductor or using a harmonic coefficient generator in the type described in U.S. Pat. No. 2,752,092.

$$M^2 = 8\left(\frac{V_{a2}V_{b1}}{2V_{a2}V_{b1} - V_{a0}V_{b1} - V_{a1}V_{b0}}\right) \quad \text{EQUATION 3}$$

$$M^2 = 8\left(\frac{V_{a2}V_{b2}}{2V_{a2}V_{b2} - V_{a0}V_{b2} - V_{a2}V_{b0}}\right), \quad \text{EQUATION 4}$$

$$\tan(\Delta) = \frac{V_{a1}M}{4V_{a2}}, \quad \text{EQUATION 5}$$

$$\tan(\Psi) = \frac{1}{2}(U - \sqrt{U^2 - 4}), \text{ and} \quad \text{EQUATION 6}$$

$$U = -2\cos(\Delta)\left(1 + \frac{[V_{a0} - V_{a2}]M^2}{4V_{a2}}\right). \quad \text{EQUATION 7}$$

$$\sin(\Delta) = \frac{2V_{a2}}{C_a \tau M^2} \quad \text{EQUATION 8}$$

$$[\tan(\Psi)]^2 = 1 - \frac{V_{a1}}{C_a M} \quad \text{EQUATION 9}$$

$$M^2 = 8\left(\frac{V_{a2}V_{b1}}{2V_{a2}V_{b1} - V_{a0}V_{b1} + V_{a1}V_{b0}}\right) \quad \text{EQUATION 10}$$

$$C_a = \left(\frac{4V_{a2} + V_{a1}M + (V_{a0} - V_{a2})M^2}{2M^2}\right) \quad \text{EQUATION 11}$$

proto.cpp

/* This code is written to acquire data with a D50 data acquisition board manufactured by Metrabyte Co.
The code will acquire data from the modulation ellipsometer and convert it to Psi and Delta.

For the executable program to be complete and functional at all this file (proto.cpp) should be linked with d50.cpp and show.cpp.
The code is to be compiled with a Borland C++ compiler or compatible written by *Hassanayn Machlab* June-1992
*/

```cpp
#include<dos.h>
#include<complex.h>
#include<stdio.h>
#include<iostream.h>
#include<string.h>
#include<stdlib.h>
#include<conio.h>
#include<math.h>
#include"has.h"
#include<graphics.h>
extern int D50InputInt(int *Int);
extern void GetError();
extern FILE *D50;
FILE *out;
extern graphinit();
extern void DAS50(void);
extern void plotfourier(float *,int,int,int,int,int);
extern complex *getfourierc(float *rawdata,int);
extern int  D50Output(char *Str);
int fileread(void);
int directread(float *);
float *GetPsiDelta(int,char);
void initD50(void);
void AcquireAndSave(void);
void insitu(void);
int datapts;
int numwaves=1;
float channel0[2030],channel1[2030],DCoffset0,DCoffset1,m=0;
int data[2030];
extern char filename[20];
main()
{    complex *gfcch0,*gfcch1;
     char fileout[20],ch;
     int channels=0,choice,j=0;
     initD50();
dc:

// get background noise before acquiring data printf("Block the light beam for dc offset measurement...\n");
        printf("push any key to take measurement\n");
```

```c
        getch();
        directread(channel0);           // read data from channel 0
        gfcch0=getfourierc(channel0,datapts);   // fourier transform the data
        DCoffset0=abs(gfcch0[0]);
        printf(" DCoffset0=%f\n",DCoffset0);
        directread(channel1);           // read data from channel 1
        gfcch1=getfourierc(channel1,datapts);   // fourier transform the data
        DCoffset1=abs(gfcch1[0]);
        printf(" DCoffset1=%f\n",DCoffset1);

printf("\nPush any key to continue acquiring data\n");
        getch();

// start acquiring data
menu:   clrscr();
        printf("DATA ACQUISITION FROM ME\n\n");
        printf("1.acquire data thru interface or read from file\n");
        printf("2.acquire several data and save results to a file\n");
        printf("3.acquire one set of data \n");
        printf("4.display file contents \n");
        printf("5.measure dc offset\n");
        printf("6.insitu\n");
        printf("99. exit\n");
        scanf("%d",&choice);
reask:
        if(!(choice == 99 || choice == 4))
        {
          printf("enter the number of cycles to average at (max=100)\n");
          scanf("%d",&numwaves);
        }
        if(numwaves>100)goto reask;

switch(choice)
        {
        case 1:
          channels=fileread();
          GetPsiDelta(channels,'0');
          goto menu;
        case 2:
          printf("enter filename to store the data in\n");
          scanf("%s",fileout);
          out=fopen(fileout,"w+");
          AcquireAndSave();;
          fclose(out);
          goto menu;
```

```c
case 3:
  if (D50Output("Set Channels=0\n")) GetError();
  directread(channel0);
  if (D50Output("Set Channels=1\n")) GetError();
  directread(channel1);

// plot data
      graphinit();
      plotfourier(channel0,datapts,25,290,25,215);
      plotfourier(channel1,datapts,310,600,25,215);
      wind ch00(40,290,260,450,0,0,0,0);
      ch00.plotreal(channel0,datapts,"channel-0");
      wind ch1(310,600,260,450,0,0,0,0);
      ch1.plotreal(channel1,datapts,"channel-1");
      getch();
       closegraph();
channels=2;
GetPsiDelta(channels,'0');
getch();
goto menu;

case 4:
  clrscr();
  printf("enter filename to display \n");
  scanf("%s",fileout);
  if((out=fopen(fileout,"r")) == NULL)
  { printf("error opening %s\n",fileout);
    getch();
    goto menu;
  }
  j=1;
  while(fscanf(out,"%c",&ch) != EOF)
  {
  if(ch == '\n')j++;
  if(j == 25)
      {j=1;
       getch();    // display 25 lines at a time
      }
  printf("%c",ch);
  }
  fclose(out);
  getch();
  goto menu;

case 5:
  goto dc;
```

```
case 6:
  printf("enter filename to store the data in\n");
  scanf("%s",fileout);
  out=fopen(fileout,"w+");
    insitu();
  fclose(out);
    goto menu;

case 99:
   printf("\nprogram terminated by user !!\n");
   fclose(D50);
   exit(0);
default:
   goto menu;
} return(0);
}

// Read raw data directly from data acquiaition board without using supplied software int directread(float *channel)
{
        int status,i,bits,channels;
        unsigned int seg,off;
        float fsv;
        char cmd[100];
        rewind(D50);
        if ( D50Output("Clear\n")) GetError();     // Clear the communication buffer
        if ( D50Output("stop\n")) GetError();

datapts=numwaves*20;
        sprintf(cmd,"Set Samples=%d\n",datapts+20);
        if (D50Output(cmd)) GetError();

// acquire data if (D50Output("Acquire \n")) GetError();   // Start the Trace
        do {
           if (D50Output("REad Status\n")) GetError();    //Wait for Trace to be done
           if (D50InputInt(&status)) GetError();
           printf("++++\r");
        }while ((status & 0x18) != 0x18);
```

```c
// tranfer data to array if (D50Output("SET ADD=4 \n")) GetError();
        sprintf(cmd,"TRAnsfer %u %u %d\n",FP_SEG(data),FP_OFF(data),datapts);
        if (D50Output(cmd)) GetError();

// convert binary numbers to equivalent voltages if (D50Output("read range\n")) GetError();
        if (D50InputInt(&status)) GetError();
        switch(status)
        { case 0: fsv=2.5; bits=pow(2,11); break;    //bipolar
          case 1: fsv=5;   bits=pow(2,11); break;
          case 2: fsv=10;  bits=pow(2,11); break;
          case 3: fsv=5;   bits=pow(2,12); break;    //unipolar
          case 4: fsv=10;  bits=pow(2,12); break;
        }
        for(i=0;i<datapts;i++)
        {
        channel[i]=-fsv*data[i]/bits; // convert to voltage
        } channels=1;
        return channels;

}

// initialize data acquisition board void initD50()
{
        D50 = fopen( "$DAS50","r+");            // open DAS50 for output and input
        if ( D50Output("Clear\n")) GetError();  // Clear the communication buffer
        if ( D50Output("stop\n")) GetError();

if (D50Output("Set Channels=0\n")) GetError();
if (D50Output("Set Samples=48\n")) GetError(); // should be in steps of 16
if (D50Output("Set Range= +-10v\n")) GetError();
if (D50Output("Set Trigger Mode=5\n")) GetError();//6- digital negative edge
if (D50Output("Set Start=After\n")) GetError();
if (D50Output("Set Rate= Int 1e6\n")) GetError();
}
```

```c
//*********insitu*********************
// read data continuosly and store to a file void insitu(void)
{   int channels,parameter,numpoints,j;
    unsigned _delay;
    char ans,title[20];
    float *PARAMS;
reask:
    clrscr();
    printf("Display quantities or graph ('q' or 'g')?\n");
    printf("enter 'e' to exit\n");
    ans=getch();
    printf("enter total number of points to acquire \n");
    scanf("%d",&numpoints);
    printf("\nenter delay between points in milliseconds\n");
    scanf("%u",&_delay);

if(ans=='g')
    {
param:
    clrscr();
    printf("0. graph Delta from channel0\n");
    printf("1. graph Psi from channel0\n");
    printf("2. graph Delta from channel1\n");
    printf("3. graph Psi from channel1\n");
    scanf("%d",&parameter);

if(parameter == 0)
    {
        strcpy(title,"Delta-channel 0");
        if (D50Output("Set Channels=0\n")) GetError();
    }
if(parameter == 1)
    {
        strcpy(title,"Psi-channel 0");
        if (D50Output("Set Channels=0\n")) GetError();
    }
if(parameter == 2)
    {
        strcpy(title,"Delta-channel 1");
        if (D50Output("Set Channels=1\n")) GetError();
    }
if(parameter == 3)
  {
        strcpy(title,"Psi-channel 1");
        if (D50Output("Set Channels=1\n")) GetError();
   }
if(parameter <0 || parameter >3)goto param;
```

```
graphinit();
wind acquire(40,600,40,450,0,0,0,0);
acquire.plotinsitu(numpoints,title,parameter,_delay);  //0->prints Delta
getch();
closegraph();
goto end;
} if(ans=='q')
{
j=0;
while(j<=numpoints)
{
    if (D50Output("Set Channels=0\n")) GetError();
    directread(channel0);
    if (D50Output("Set Channels=1\n")) GetError();
    directread(channel1);

channels=2;
    PARAMS=GetPsiDelta(channels,' ');
  printf("%5.2f %5.2f %5.2f %5.2f %6.4f %6.4f %6.4f\n",
  PARAMS[0],PARAMS[1],
  PARAMS[2],PARAMS[3],PARAMS[5],PARAMS[4],
  PARAMS[6]);
  fprintf(out,"%5.2f %5.2f %5.2f %5.2f %6.4f %6.4f %6.4f\n",
  PARAMS[0],PARAMS[1],
  PARAMS[2],PARAMS[3],PARAMS[5],PARAMS[4],
  PARAMS[6]);
 delay(_delay);
 j++;
}
printf("\n Done!!, push any key to continue \n");
getch();
goto end;
} if(ans=='e')goto end;

if(ans != 'g' && ans != 'q' && ans != 'e')
 goto reask;
 end:;
}

/* reads data from the DA card through directread() and converts them to Psi and
Delta. Then saves data in desired file.
*/
```

```c
//*********acquireandsave***************
void AcquireAndSave(void)
{       int channels;
        char ch='0',chtemp;
        float inread,*PARAMS;
        clrscr();
        chtemp=ch;
        while(inread != -1)
        {
        printf("\n enter variable reading, enter -1 to quit\n");
        scanf("%f",&inread);
        if(inread != -1)
          {
          clrscr();
                printf("enter channel '0','1'or '2' for 0 & 1\n");
                ch=getch();
                if(ch != '0' && ch!= '1' && ch!= '2')ch=chtemp;
                chtemp=ch;
                if(ch == '0')
                {
                if (D50Output("Set Channels=0\n")) GetError();
                directread(channel0);
                }
                if(ch == '1')
                {
                if (D50Output("Set Channels=1\n")) GetError();
                directread(channel1);
                }
                if(ch == '2')   // read data from both channels
                {
                if (D50Output("Set Channels=0\n")) GetError();
                directread(channel0);
                if (D50Output("Set Channels=1\n")) GetError();
                directread(channel1);
                channels=2;
                } printf("channel= %c\n",ch);

PARAMS=GetPsiDelta(channels,ch);   // convert to Psi and Delta

/*************** store data in a file**********/
        fprintf(out," %c %5.2f %5.2f %5.2f %5.2f %5.2f %6.4f %6.4f %6.4f\n",
        ch,inread,PARAMS[0],PARAMS[1],
        PARAMS[2],PARAMS[3],PARAMS[5],PARAMS[4],
        PARAMS[6]);
          }
        }
}
```

//*******GetPsiDelta***************
/* This subdirectory converts the raw data to Psi and Delta.
 for this subroutine Channel0,channel1 and datapts have to be declared outside main
*/
```c
float *GetPsiDelta(int channels,char ch)
{
        complex *gfcch0,*gfcch1;
        double magch0[20],magch1[20],mcalc1,mcalc2,mcalc;
        double va0,va1,va2,va3,va4,vb0,vb1,vb2,vb3,vb4;
        float U,Delta,Tau,Tau2,PARAMS[10],ca,dummy;
        int signva1,signva2,signvb1,signvb2;
        int j;
        char *p,mp[10];
if(ch !=' ')   // for insitu
{
// modulation..m.  Used in calculations.
    mp[0]=6;
    printf("\n enter modulation (in waves), default = %6.4f radians\t",m);
    p=cgets(mp);       //if return is pushed m keeps a default value
    printf("\n");
    if(mp[1] != 0)
     {
     m=atof(p);
     m=m*2*3.14159265;      // convert m from waves to rad
     }
}
else
     m=.1*2*3.14159265;     // convert m from waves to rad
PARAMS[5]=m;
/*****************/
/*  channel 0   */
/*****************/
        if(channels==2 || channels==1 && ch=='0')
{
// get the fourier coefficints and put them in gfcch0.

gfcch0=getfourierc(channel0,datapts);   // fourier transform the data
        for (j=0;j<5;j++)
        {
        magch0[j]=abs(gfcch0[j]);
          if(ch !=' ')    // for insitu
printf("va[%d] = %lf phase=%lg re=%lg im=%lg\n",j,magch0[j],
       (atan(imag(gfcch0[j])/real(gfcch0[j])))*180/M_PI,real(gfcch0[j]),
       imag(gfcch0[j]));
        }
```

```
// find the sign for the first and second harmonics
   signva1=+1; signva2=+1;
if(real(gfcch0[7])<0)signva1=-1;  // sign of unaveraged va1 coefficient
if(real(gfcch0[8])<0)signva2=-1;  // sign of unaveraged va2 coefficient
```

/* assign values for clarity. These are the final values of the fourier coefficients used in the calculations of Psi and Delta */

```
va0=magch0[0]-DCoffset0;
  va1=magch0[1]*signva1;        va2=magch0[2]*signva2;
  va3=magch0[3]*(-1)*signva1;   va4=magch0[4]*(-1)*signva2;
if(ch !=' ')   // for insitu
  printf("Va0=%lf",va0);
```

/*————————
results for channel 0
————————*/

// Calculation of DELTA

```
        Delta=atan(0.25*va1*m/va2);
if(ch !=' ')    // for insitu
        if(signva1==-1 && signva2==+1)
           printf("\nDelta-a= %f deg\t",(M_PI+Delta)*180/3.14159265);
        else
           printf("\nDelta-a= %f deg\t",Delta*180/3.14159265);
```

// Calculation of U and Tau

```
U=0.5*cos(Delta)*((va0*m*m/va2)-m*m+4);  // channel 'a' calculation
        if(U<=-2)U=U*(-1);
     if(ch !=' ')    // for insitu
        printf("U= %f\t",U);
        if(U>=2)
        {
        Tau=-0.5*sqrt(U*U-4)+0.5*U; // channel 'a' calculation
     if(ch !=' ')    // for insitu
        printf("psi-a= %f\n\n",atan(Tau)*180/M_PI);
        }
        else
        {
        Tau=9999;
     if(ch !=' ')    // for insitu
        printf("Tau is complex\n");
        } if(signva1==-1 && signva2==+1)Delta=M_PI+Delta;
        if(signva1==+1 && signva2==-1)Delta=2*M_PI+Delta;
        if(signva1==-1 && signva2==-1)Delta=M_PI+Delta;
```

PARAMS[0]=Delta*180/M_PI; PARAMS[1]=atan(Tau)*180/M_PI;
}

/***************/
/* channel 1   */
/***************/

```c
if(channels == 2 || channels==1 && ch=='1')
{
        gfcch1=getfourierc(channel1,datapts);     // fourier transform the data
        for (j=0;j<5;j++)
        {
        magch1[j]=abs(gfcch1[j]);
if(ch !=' ')   // for insitu
printf("vb[%d] = %lf phase=%lg re=%lg im=%lg\n",j,magch1[j],
        (atan(imag(gfcch1[j])/real(gfcch1[j])))*180/M_PI,real(gfcch1[j]),
        imag(gfcch1[j]));
        }

// find the sign for the first and second harmonics
        signvb1=+1; signvb2=+1;
        if(real(gfcch1[7])<0)signvb1=-1; // sign of unaveraged vb1
        if(real(gfcch1[8])<0)signvb2=-1; // sign of unaveraged vb2

// assign values for clarity
   vb0=magch1[0]-DCoffset1;
   vb1=magch1[1]*signvb1;           vb2=magch1[2]*signvb2;
   vb3=magch1[3]*(-1)*signvb1;      vb4=magch1[4]*(-1)*signvb2;
if(ch !=' ')   // for insitu
   printf("Vb0=%lf",vb0);
```

/*——————————
results from channel1
——————————*/

```c
  // calculation of Delta

Delta=atan(0.25*vb1*m/vb2);
        if(ch !=' ')   // for insitu
        if(signvb1==+1 && signvb2==-1)
           printf("\nDelta-b= %f deg\t",(M_PI+Delta)*180/3.14159265);
        else
           printf("\nDelta-b= %f deg\t",Delta*180/3.14159265);
```

```c
// calculation of U and Tau
    U=0.25*cos(Delta)*(-(vb0*m*m/vb2)+m*m-4); // channel 'b' calculation
    if(U<=-1)U=U*(-1);
if(ch !=' ')   // for insitu
    printf("U= %f \t",U);
    if(U>=1)
    {
    Tau=U-sqrt(U*U-1);
if(ch !=' ')   // for insitu
    printf("psi-b= %f\n\n",atan(Tau)*180/M_PI);
    }
    else
    {
    Tau=9999;
if(ch !=' ')   // for insitu
    printf("Tau is complex\n");
    } if(signvb1==+1 && signvb2==-1)Delta=M_PI+Delta;
    if(signvb1==-1 && signvb2==+1)Delta=2*M_PI+Delta;
    if(signvb1==-1 && signvb2==-1)Delta=M_PI+Delta;

/****************************************************/

PARAMS[2]=Delta*180/M_PI;PARAMS[3]=atan(Tau)*180/M_PI;
}
    if(channels ==2)
    {
// claculation of modulation
    mcalc=8*va2*vb2/(2*va2*vb2-va0*vb2-va2*vb0);
    mcalc1=8*(va2*vb1/(2*va2*vb1-va0*vb1-va1*vb0));
    if(mcalc<0 || mcalc1 <0)
    {
    if(ch !=' ')   // for insitu
    {
    if(mcalc<0)
    printf("\nm calculated from v2's & v0's is a complex number,sqrt(%lf)\n",mcalc);
    if(mcalc1<0)
    printf("\nm calculated from v1's & v2's & v0's is a complex number,sqrt(%lf)\n",mcalc);
    }
    }
    else
    {
```

```
        mcalc=sqrt(mcalc);
    if(ch !=' ')    // for insitu
        {
        printf("m calculated from v2's & v0's m= %lf \n",mcalc/(2*M_PI));
        printf("m calculated from v1's,v2's & v0's m= %lf \n",mcalc1/(2*M_PI));
        }
        PARAMS[4]=mcalc;
        PARAMS[6]=mcalc1;

}
} return PARAMS;

}

/* the following subroutine reads data from files ganerated by the software
supplied with the data acquisition board */ int fileread()
{
  char a[50];
  int numsamples,j,m,e,bits,jj,throwpts,i,channels;
  float fsv,b,dummy,max;
  double rate;
  long pos,mant,expon;
  FILE *in;

reask:
    DAS50();

if((in=fopen(filename,"r+"))==NULL)
    {
    printf("error, couldn't open %s. Push any key to continue\n",filename);
    getch();
    goto reask;
    } a[0]='\0';
  while(strcmp(a,"SampleSetSize"))fscanf(in,"%s",&a);
  fscanf(in,"%d",&numsamples);
  while(strcmp(a,"RateMantissa"))fscanf(in,"%s",&a);
  fscanf(in,"%ld",&mant);
```

```
while(strcmp(a,"RateExponent"))fscanf(in,"%s",&a);
fscanf(in,"%ld",&expon);
while(strcmp(a,"Channels"))fscanf(in,"%s",&a);
fscanf(in,"%d",&channels);
rate=((double)mant*pow(10,(double)expon))*channels;
while(strcmp(a,"Polarity"))fscanf(in,"%s",&a);
fscanf(in,"%s",&a);
if(!(strcmp(a,"Bipolar")))bits=pow(2,11);
if(!(strcmp(a,"Unipolar")))bits=pow(2,12);
while(strcmp(a,"FSMantissa"))fscanf(in,"%s",&a);
fscanf(in,"%d",&m);
while(strcmp(a,"FSExponent"))fscanf(in,"%s",&a);
fscanf(in,"%d",&e);
fsv=m*pow(10,e);    // calculation of full scale voltage clrscr();
printf("enter number of waves\n");

scanf("%d",&numwaves);
datapts=(1/(rate*50e3))*numwaves;
if(numsamples<datapts)
{
printf("not enough number of samples\n");
fclose(in);
exit(0);
} while(strcmp(a,"Data"))fscanf(in,"%s",&a);
graphinit();
    for(j=0;j<4;j++)fscanf(in,"%f",&dummy);
if(channels==1)
{
    for(j=0;j<datapts;j++)
    {
    fscanf(in,"%f",&channel0[j]);
    channel0[j]=-fsv*channel0[j]/bits; // convert to voltage
    } plotfourier(channel0,datapts,25,600,25,215);
```

```
wind ch0(40,600,260,450,0,0,0,0);
ch0.plotreal(channel0,datapts,"channel-0");
} if(channels==2)
{ for(j=0;j<datapts;j++)
    {
    fscanf(in,"%f,%f\n",&channel0[j],&channel1[j]);
    channel0[j]=-fsv*channel0[j]/bits;  // convert to voltage
    channel1[j]=-fsv*channel1[j]/bits;  // convert to voltage
    }
    plotfourier(channel0,datapts,25,290,25,215);
    plotfourier(channel1,datapts,310,600,25,215);
    wind ch00(40,290,260,450,0,0,0,0);
    ch00.plotreal(channel0,datapts,"channel-0");
    wind ch1(310,600,260,450,0,0,0,0);
    ch1.plotreal(channel1,datapts,"channel-1");

}
    fclose(in);
    getch();
    closegraph();
    return channels;
}
```

In FIG. 2, there is a slight modification of the embodiment of FIG. 1, which is that a quarter wave compensator 15 is inserted between the first polarizer 14 and the modulator 16. This produces circularly polarized light at the modulator 16 and nearly circularly polarized light at the sample 18. The detector outputs have the same form as in the embodiments of FIG. 1. The delta and psi are determined from equations 8, 9 10 and 11.

The amplitudes of the dc and harmonic contributions may be extracted using analog or digital filters, and lock-in amplification or digital Fourier analysis. Psi and delta can be determined in the case of the embodiment of FIG. 1 from equations 3, 4, 5, 6 and 7. In the case of the embodiment of FIG. 2, equations 8, 9, 10 and 11 may be used to determine psi and delta. In these equations M is the modulation amplitude.

It can be determined from these equations that psi and delta are independent from the calibration errors. As can be determined from a conventional Jones matrix, psi and delta are functions of the sine and cosine of the modulation angle. Thus, for modulation angles that are very small, the sine is so small that the terms containing the sine are negligible and the terms containing the cosine are substantially equal to one. Because of this, for small angles of modulation, the effect caused by misalignment does not affect the end result in any significant way. Generally, the modulation angle which results in independence from alignment errors is less than ten degrees and preferably under five degrees.

In FIG. 3, there is shown another embodiment 10A of the ellipsometer substantially the same as the embodiment 10 shown in FIG. 1 except that it incorporates an additional amplitude modulation stage to reduce noise. In embodiment 10A, a source of amplitude modulation signals 46 modulates the source of light 12A, which may be a laser, in intensity so as to provide an intensity modulated light source to the polarizer 14 rather than unmodulated light from the source of light 12 as in the embodiment 10 of FIG. 1. The light signal after passing through the dual analyzer is demodulated before being applied to the analog to digital converter system 36 by being applied to a mixer 42 which is also connected to a function generator or to the source 46 to mix the signals and then being applied to a low pass filter 40 in a demodulator 38. This results in a lower noise signal being applied to the converter.

This amplitude modulation of the light source at a frequency $f_c$, called the carrier frequency, which is larger than the frequency of polarization modulation, when added to the phase modulation, causes all signals to be carried at high frequency, thus reducing noise and, particularly, eliminating dc offset or drift voltages. The original construction and operation of the SME remains as described above in connection with the embodiment of FIG. 1.

In the operation of the embodiment of FIG. 3, the source is amplitude modulated at high frequency. Amplitude modulation can be achieved by direct modulation of a laser source or by use of an external modulator such as an acousto-optic or electro-optic modulator. The amplitude modulated light passes through the polarizer 14 and polarization modulator 26, reflects from or passes through the sample 18, and then passes through the split polarizer.

The orthogonally polarized components of the light beam are converted to electrical signals by the two detectors 32. These signals are composed of the amplitude modulated carrier signal at frequency $f_c$ with sidebands at the polarization modulation frequency and harmonics as well as undesired dc and ac noise and interference.

The electrical signals are demodulated by standard demodulation techniques, such as synchronous (coherent) detection implemented as in FIG. 3. Demodulation retains only those signals at $f_c$ and its sidebands and rejects all signals that are far from $f_c$. This allows the detection of the information carrying signal and the rejection of the noise and dc offset signals. The signal at fc is removed by the low pass filter 40.

Equations 3 to 11 are correct to second order in the modulation amplitude M. The accuracy of delta and tan. psi may be improved arbitrarily by using higher harmonics of the two signals Va and Vb. Alternate expressions such as shown in equations 3 and 4 for $M^2$ permit accurate calculation of delta and tan. psi when particular terms of the Fourier expansions (e.g. the nth term $Va_n$ or $Vb_n$) have a low signal-to-noise. Preferably delta and tan. psi are calculated to the fourth order although better precision is obtained by higher order calculations (use of more terms of the Fourier expansion).

In the preferred embodiment, the sources 12 or 12A are each a 5 milliwatt diode laser sold as model LAS-200-670-5 by Laser Max, Inc., 207 Tremont St., Rochester, N.Y. 14608, although a monochrometer with a diffraction grating may be used. The polarizer is a glan-laser polarizer, model MGT25S5 and the split analyzer is a prism polarizer, model MW2A-10-20, both of which are sold by Karl Lambrecht, 4204 N Lincoln Ave., Chicago, Ill. 60618. The compensator used in the embodiment of FIG. 2 is a precision quarter wave plate sold under the catalog no. 02WRQ001-670 by Melles Griot, 1770 Kettering Street, Irvine, Calif. 927124-6463. The modulator is a photoelastic phase modulator system sold under model numbers PEM-90 for the system and PEM-90C for the controller, I/FS50 for the head and with AR coatings by Hinds Corp., 5250 N. E. Elam Young Parkway, Hillsboro, Oreg. 97124-6463. The two detectors are silicon photodiodes, model SD100-13-13-022 sold by Silicon Detector Corp., 1240 Avenida Acaso, Camarillo, Calif. 93010 and the analog to digital converter board is an analog to digital data acquisition board for a personal computer sold under the model DAS-50 by Keithly/Metrabyte, 440 Miles Standish Blvd., Taunton, Mass. 02780.

As can be understood from the above description, this ellipsometric technique has several advantages, such as: (1) it can measure a changing environment, such as for example a surface that is in use such as in a space craft or the like; and (2) there is less time necessary for calibrating the instrument to different surfaces.

Although a preferred embodiment of the invention has been described with some particularity, many modifications and variations in the invention are possible within the light of the above teachings. Therefore, it is to be understood that, within the scope of the appended claims, the invention may be practiced other than as specifically described.

What is claimed is:

1. A method of ellipsometry comprising the steps of: polarizing a light beam; applying the polarized light to a sample; developing signals representing orthogonal planes of polarization from the light after it has interacted with the sample, Whereby two polarized light signals are obtained; and calculating constants, psi and delta, of the sample from the two resulting polarized light signals, wherein a phase modulator phase modulates the light within a range of no more than ten degrees, whereby calibration errors are sufficiently small to be disregarded.

2. A method in accordance with claim 1 in which the two signals are expanded by Fourier analysis and the coefficients thereof utilized to calculate psi and delta.

3. A method in accordance with claim 1 in which the light beam is amplitude modulated before being transmitted to the sample and the two signals are demodulated to provide noise reducing synchronous demodulation.

4. A method in accordance with claim 1 in which the beam of light is plane polarized.

5. A method in accordance with claim 1 in which the beam of light is circularly polarized.

6. Apparatus comprising: means for polarizing a light beam; means for applying the polarized light to a sample; means for developing signals representing orthogonal planes of polarization from the light after it has interacted with the sample, whereby two polarized light signals are obtained; and means for calculating constants, psi and delta, of the sample from the two resulting polarized light signals, wherein a phase modulator phase modulates the light within a range of no more than ten degrees, whereby calibration errors are sufficiently small to be disregarded.

7. Apparatus in accordance with claim 6 further including means for expanding the two signals by Fourier analysis and using the coefficients thereof to calculate psi and delta.

8. Apparatus in accordance with claim 6 further including means for amplitude modulating the beam of light before transmitting it to the sample and demodulating the two signals to provide noise reducing synchronous demodulation.

9. Apparatus in accordance with claim 6 further including means for plane polarizing the beam of light.

10. Apparatus in accordance with claim 6 further including means for circularly polarizing the beam of light.

* * * * *